United States Patent [19]

Shiba et al.

[11] 4,146,798
[45] Mar. 27, 1979

[54] INK FEED VOLUME MEASURING DEVICE

[75] Inventors: Noriyuki Shiba, Tokyo; Shu Yoshida, Kiyose, both of Japan

[73] Assignee: Tokyo Kikai Seisakusho, Ltd., Tokyo, Japan

[21] Appl. No.: 773,291

[22] Filed: Mar. 1, 1977

[30] Foreign Application Priority Data

Mar. 12, 1976 [JP] Japan .............................. 51-30588[U]

[51] Int. Cl.² ........................................... G01N 21/30
[52] U.S. Cl. .................................. 250/571; 356/435; 356/443
[58] Field of Search ............... 250/484, 559, 562, 571, 250/572; 356/201–206; 313/498

[56] References Cited

U.S. PATENT DOCUMENTS

| | | | |
|---|---|---|---|
| 2,333,759 | 11/1943 | Akelaitis | 356/202 |
| 3,241,472 | 3/1966 | Robertson | 313/498 |
| 3,252,035 | 5/1966 | Buck | 313/498 |
| 3,790,275 | 2/1974 | Huboi et al. | 356/206 |

*Primary Examiner*—David C. Nelms

[57] ABSTRACT

An ink feed measuring device comprising a luminous plate and a light receiving plate constructed so as to hold a photographic film of a printed matter between the two plates, the luminous plate having one or more electro-luminescent plates and the light receiving plate having a plurality of photoelectric elements corresponding to the sectioned areas of the photographic film, wherein ink feed volume corresponding to each sectioned area of the photographic film is measured based on the amount of light transmitted through the sectioned areas of the film.

7 Claims, 11 Drawing Figures

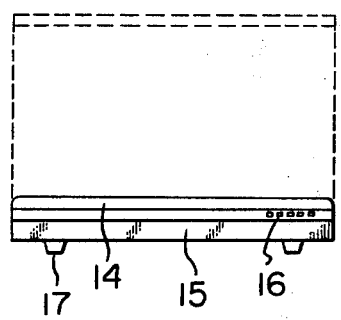
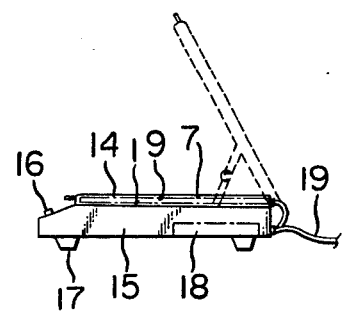
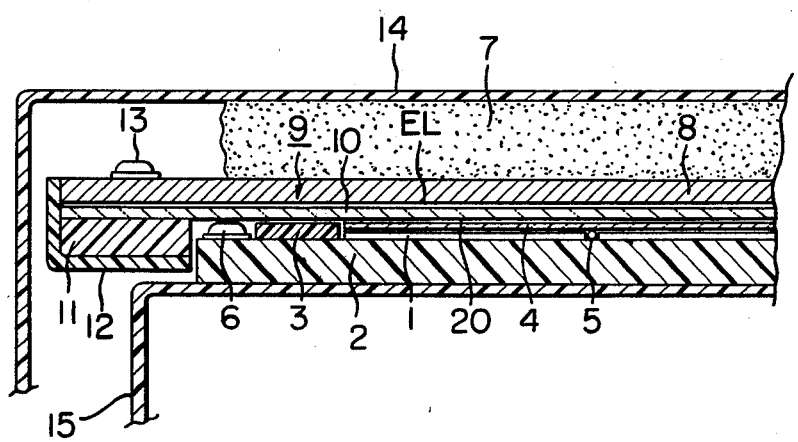
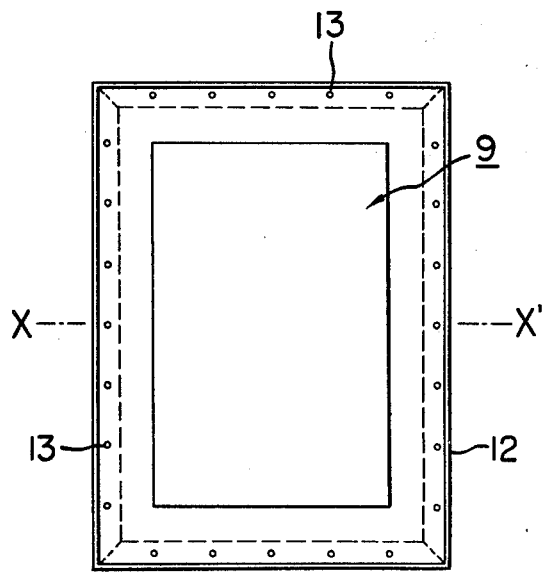
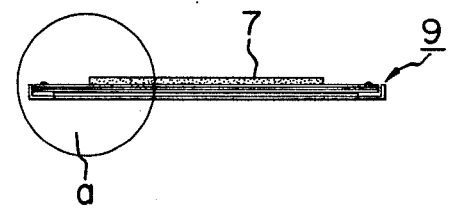

INK FEED VOLUME MEASURING DEVICE

BACKGROUND OF THE INVENTION

1. Field of the Invention

This invention relates generally to an ink feed measuring device, and more specifically to an ink feed measuring device wherein a luminous plate and a light receiving plate are disposed so as to closely contact with each other, and the amount of light transmitted through a photographic negative film (or a positive film . . . hereinafter referred to as a film) of a newspaper held between the luminous and light receiving plates is measured by reading out a change in electromotive force generated on the light receiving plate, and a surface source is employed as a light source to ensure uniform brightness on the luminous plate.

2. Description of the Prior Art

In a printing press, for example, a newspaper printing press, which prints a large number of copies at a high speed, a uniform printing finish is strongly desired on each and every sheet of newspaper. However, even in a single page of newspaper, there are some portions where a large amount of ink is required and other portions where a small amount of ink is needed, depending on the nature of news. Therefore, when printing such a newspaper page in succession, supplying the same quantity of ink over the entire page may cause blackening due to overfeeding of ink in some parts and thinning due to shortage of ink in other parts. Consequently, there is a need to control the ink feed amount by measuring the required amount of ink for a given page of newspaper as precisely as possible.

Heretofore, a plurality of incandescent lamps or straight-tube fluorescent lamps have been used as the light source of a measuring device of this type. The luminous plate using these light sources, which are a combination of point or line light sources, tend to be uneven in brightness. In particular, the intensity of illumination on the luminous plate becomes uneven because the use of a plurality of light sources makes a difference in the luminance of individual light sources with the lapse of time. Uneven intensity of illumination on the luminous plate is quite an unwanted phenomenon for a measuring device of this type which controls the feed amount of ink to a printing press with measurements of the change of electromotive force corresponding to the change of the amount of light. Furthermore, incandescent lamps or fluorescent lamps used in such a device are considerably large in size and require appliances or fixtures in some form or other to light them. In addition, since these light sources produce heat, the conventional luminous plates consisting of a plurality of light sources of these types tend to be of large size and have limitations in their construction.

SUMMARY OF THE INVENTION

This invention is intended to solve these problems. An object of this invention is to provide an ink feed measuring device wherein a surface light source is used as its light source to ensure uniform intensity of illumination on the luminous plate, and the use of an extra-thin illuminant which does not involve generation of heat enables a remarkably thin luminous plate, thus making the ink feed measuring device small-sized, light-weight, and easy to handle while retaining high measuring performances. Another object of this invention is to provide an ink feed measuring device of preferred construction. Still another object of this invention is to provide an ink feed measuring device which is designed to eliminate the effect on measurements of uneven brightness concomitant with the shape of the surface source housing by employing such a construction that permits the surface source, the film and the light receiving plate to be virtually in close contact with each other.

BRIEF DESCRIPTION OF THE DRAWINGS

FIGS. 1A and 1B are views in front and side elevation, respectively, illustrating the external appearance of an ink feed volume measuring device embodying the present invention.

FIG. 2 is a partial section of the film holder portion of the embodiment shown in FIG. 1.

FIGS. 3a and 3b are top and sectional views showing the luminous plate of the embodiment shown in FIG. 1.

DETAILED DESCRIPTION OF THE EMBODIMENT

Figure 4:
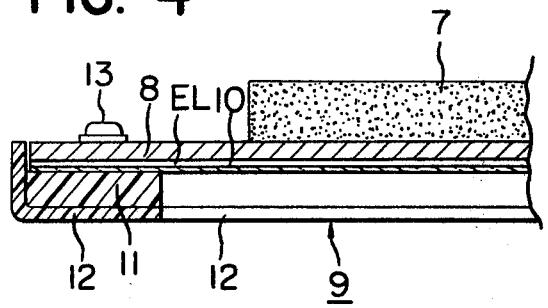
FIG. 4 is an enlarged sectional view of the part a in the section view of FIG. 3.

In FIGS. 1A and 1B, numeral 1 refers to a light receiving plate, 7 to a sponge rubber, 9 to a luminous plate, 10 to a top cover, 15 to a base box, 16 to a pushbutton, 17 to legs, 18 to an electric circuit portion, 19 to a power cord.

The luminous plate 9 and the cushioning sponge rubber 7 are fixed to the top cover 14, a side of which is hinged to a side of the base box 15 so that the top cover 14 can be opened and closed at an angle of about 60 degree above the base box 15. When placing a photographic film of a newspaper to be measured, the top cover 14 is opened, and the film to be measured is placed on the light receiving 1 fixed to the base box 15. After that, when the top cover 14 is closed and slightly depressed, the film is held between the luminous plate 9 and the light receiving plate 1, being in perfectly close contact with both plates.

FIG. 2 is a partially sectional view of the film holder portion consisting of the luminous and light receiving plates, which is the main part of the embodiment shown in FIG. 1.

In the figure, numeral 1 refers to a light receiving plate, as shown in FIG. 1, comprising a plurality of selenium photoelectric cells or solar batteries, or photoelectric elements, 2 to a mounting plate of the light receiving plate 1. Numeral 3 refers to a fixing frame for fixing the light receiving plate 1, 5 to separators, or insulator rods for dividing the light receiving plate 1 into a predetermined number of sectioned light receiving areas, 6 to fixing screws for fixing the mounting plate 2 to the base box, and 7 to a sponge rubber, 8 to an aluminum plate which is a part of the members of a luminous plate 9. Numeral 9 refers to a luminous plate using a thin electroluminescence (hereinafter referred to as EL) illuminant as its light source, EL to a surface illuminant plate, 10 to a light transmission plate covering the luminous plate 9, 11 to a mounting base for mounting the luminous plate 9, 12 to a mounting frame for fixing the mounting base 11, 13 to fixing screws, 14 to a top cover which can be opened upward, 15 to a base box, 20 to a newspaper film, or a photographic film of a newspaper to be measured. The figure shows a cross section of the film holer portion in which the newspaper film 20 to be measured is held in position, and the mounting plate of the light receiving plate 1 is fixed onto the base box 15 with fixing screws 6. A plurality of photoelectric elements are arranged, being separated and insulated with separators 5, and are fixed around them with the mounting frame 3 lest they should move lengthwise and breadthwise. The entire surface of the light receiving plate 1 on which a plurality of photoelectric elements are arranged is covered with a transparent acrylic plastic plate 4. With these members, is constructed the light receiving portion. On the other hand, the light source portion is constructed in the following fashion. A transparent acrylic plastic plate 10 is placed on the mounting base 11, an electroluminescence plate EL is placed on the transparent plate 10 and then an aluminum plate 8 is placed on the electroluminescence plate EL. The luminous plate 9 comprising the electroluminescence plate EL sandwiched between the transparent plate 10 and the aluminum plate 10 is fixed to the mounting frame 12 with fixing screws 13. The luminous plate 9 assembled in this manner is incorporated in the top cover 14, with the sponge rubber 7 interposed between the luminous plate 9 and the top cover 14, so that the luminous plate 9 can be opened and closed together with the top cover 14.

FIGS. 3A and 3B shows the luminous plate 9 proper. FIG. 3B is a cross section taken along the line X-X' in FIG. 3A. The luminous plate 9 comprising the electroluminescence plate EL sandwiched between the transparent acrylic plastic plate 10 and the aluminum plate 8 is held around its edges with the mounting frame 12 (see FIG. 4), and is fixed to the mounting frame 12 with fixing screws 13 via the mounting base 11. A sponge rubber 7 is placed on it so that pressing force is uniformly dispersed over the entire surface of the luminous plate 9. FIG. 4 is an enlarged sectional view of the portion a in FIG. 3B, and the like numbers in the figure correspond with the like numbers in FIG. 2.

Figure 5:
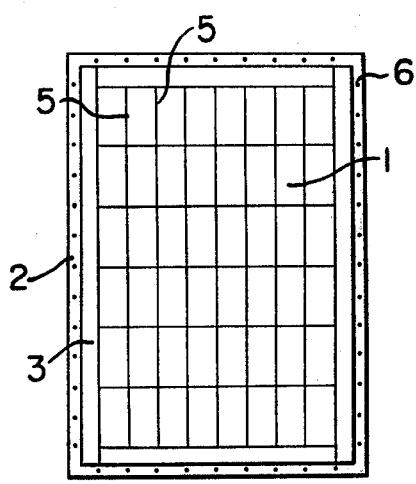
FIG. 5 is a top view illustrating the light receiving plate of the embodiment shown in FIG. 1.

FIG. 5 is the light receiving portion proper, part of which is shown in the sectional view of FIG. 2. The light receiving plate 1 of this embodiment consisting of a plurality of photoelectric elements is divided into 8 vertical rows and 6 horizontal rows, for example, as shown in FIG. 5. This is to measure the required amount of ink for each of 8 vertical rows equally dividing a whole page of a newspaper. Therefore, each photoelectric element is independently separated by separators or insulating rods 5. In this embodiment, the required amount of ink for printing a vertical row mentioned above is measured by the sum of electromotive forces generated in six photoelectric elements in that vertical row.

Figure 6A:
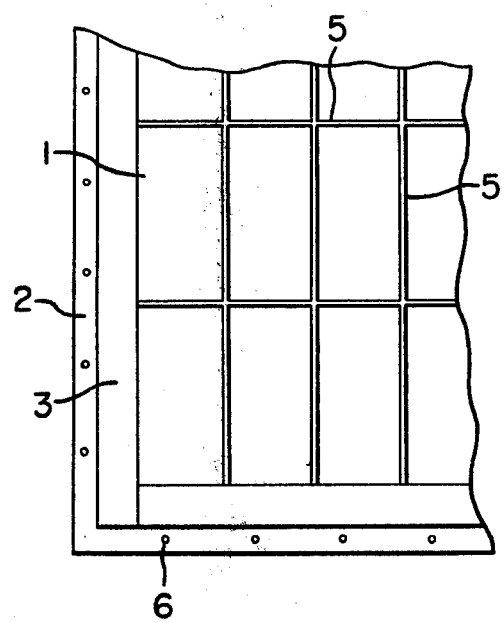
FIGS. 6a and 6b are partially enlarged and sectional views of the light receiving plate shown in FIG. 5.
Figure 7:
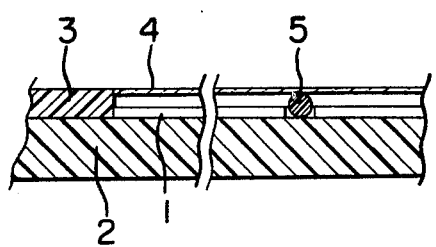
FIG. 7 is a further enlarged sectional view of a part of the sectional view in FIG. 6.
Figure 6B:
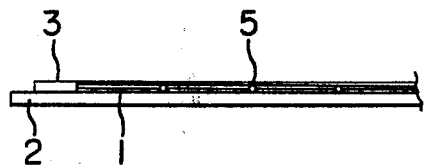

FIGS. 6A and 6B are a partially enlarged view of the light receiving plate 1 in FIG. 5 and a sectional view thereof, respectively. FIG. 7 is a further enlarged partial section of part of FIG. 6B to further clarify the construction of the light receiving plate 1. In FIGS. 6A, 6B and 7, like numerals correspond with those in FIG. 2. Individual photoelectric elements constituting the light receiving plate 1 are neatly arranged in both horizontal and vertical directions with separators, or insulating rods 5. These photoelectric elements and the transparent plate 4 placed on the light receiving plate 1 to cover it are prevented from moving sideways by fixing on all sides to the mounting plate 2 with the fixing frame 3 and fixing screws 6.

Figure 8:
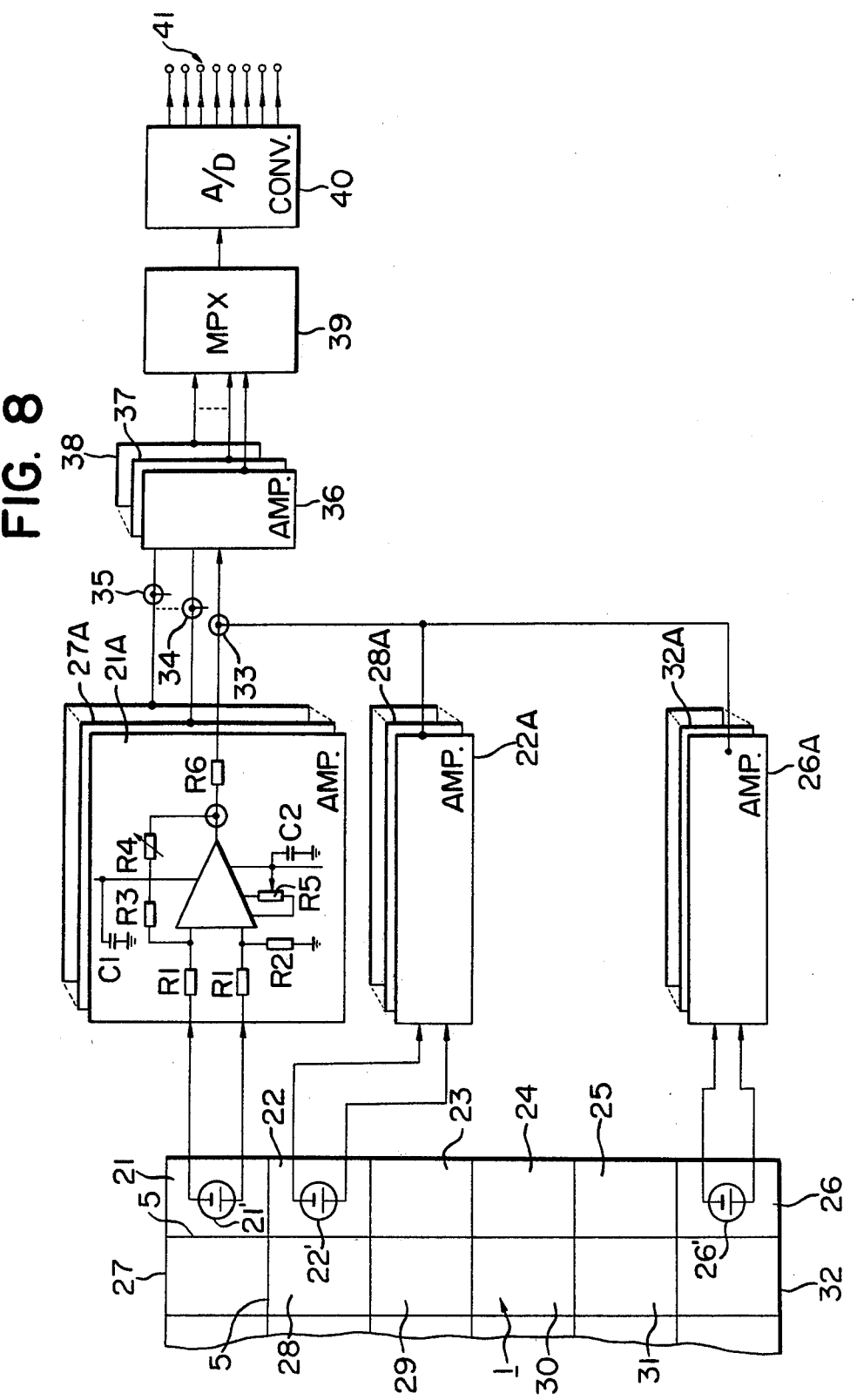
FIG. 8 is an example of electric circuit portion of the ink feed measuring device embodying this invention.

FIG. 8 shows an example of the electrical circuit in the ink feed measuring device embodying this invention. In the figure, numeral 1 refers to a light receiving plate, 5 to separators or insulator rods, 21 through 32 to photoelectric elements. 21', 22' and 26' refer to some of photoelectric elements expressed by symbols of electrical circuit elements. Photoelectric elements number 6 × 8, for example, as shown in FIG. 5, and the photoelectric elements 21 through 26 in a vertical row are separately connected to input amplifier stages 21A through 26A. Similarly, photoelectric elements 27 through 32 in the other vertical row are separately connected to input amplifier stages 27A through 32A. Each input amplifier stage can be considered to have a known circuit as typically shown by the input amplifier stage 21A. Each of the output signals from the input amplifier stages 21A, 22A, ... 26A corresponding to a vertical row is added at a junction 33 and fed to an amplifier stage 36. Similarly, each of the output signals from the input amplifier stages 27A, 28A, ... 32A corresponding to the other vertical row is added at a junction 34, and fed to an amplifier stage 37.

The outputs from amplifier stages 36, 37, ... 38 are fed to a multiplexer 39. Among those outputs, one output selected by the multiplexer 39 is converted to a digital signal in an analog/digital converter 40 and fed to one of output terminals 41. The output on the output terminal 41 is fed to a data processing equipment (not shown) which determines the required amount of ink for printing a given vertical row on a given page of newspaper to control an ink feed control valve in a rotary press (not shown).

As described above, this invention, eyeing at an unwanted effect on measurements of uneven brightness on the luminous plate of an ink feed measuring device, has enabled accurate measurement of ink feed by ensuring uniform intensity of illumination by use of an electroluminescence plate EL as the light source of the luminous plate. The use of surface light source for the light source of the luminous plate has made the light source portion much thinner than the conventional light source portion, thus making the entire measuring device of small size and lightweight and easy to handle. Furthermore, the amount of light transmitted through the film is measured in the state where the luminous plate, the film and the light receiving plate are in almost close contact with each other. This construction has the following advantage. For example, assuming the luminous plate and the film are placed facing with each other with a distance between them, brightness on the film becomes uneven due to different reflection factors of the light from various wall surfaces of the housing of the surface light source and due to the shape of the housing even when the luminous plate is composed of the surface light source, as described above. In other words, brightness varies from the central part of the circumferential part of the film. In this invention, on the other hand, measurement is made in the state where the luminous plate and the film are in almost close contact with each other. Therefore, uneven brightness caused by the shape of the light source housing does not affect the measurement results.

In addition, since the input amplifier stages 21A through 26A correspond to each of the photoelectric elements 21 through 26, for example, in a vertical row, a possible decrease in the photoelectric conversion efficiency of some photoelectric elements can be improved merely by fine adjustment of the gain of the input amplifier stage.

What is claimed is:

1. An ink feed measuring device comprising a luminous plate and a light receiving plate placed facing each other for measuring the volume of ink supply when printing a printed matter by means of measuring the amount of light transmitted through a photographic film of the printed matter, wherein the light receiving plate comprises a plurality of photoelectric elements arranged in rows and columns which are separated by insulating material, a mounting plate for mounting the photoelectric element, a fixing frame for fixing the photoelectric element at a predetermined position on the mounting plate, and a light transmitting plate which is fixed so as to cover the surface of the photoelectric elements; said luminous plate comprises at least one electroluminescent surface light source formed on a plate, and a light transmitting plate which is fixed so as to cover the surface of the electroluminescent surface light source plate; the photographic film being held directly between the two light transmitting plates, and a circuit means comprising an input amplifier stage respectively coupled to each of the photoelectric elements, the output from the amplifier stages corresponding to all the photoelectric elements from each one of the common rows being respectively coupled together, said rows being arranged along the direction of relative movement of the printed matter when printing it.

2. An ink feed measuring device as set fort in claim 1, wherein said luminous plate is constructed so as to have an area sufficient to cover the entire surface of the photoelectric elements and to extend beyond the circumferential edges of the entire surface of the photoelectric elements.

3. An ink feed measuring device as set forth in claim 2, wherein the light receiving plate comprises a plurality of photoelectric elements which are densely arranged, separated by and adjoining each other via insulating materials, a mounting plate for mounting the photoelectric elements, a fixing frame for fixing the photoelectric elements at a predetermined position on the mounting plate and a light transmitting plate which is fixed so as to cover the surface of the photoelectric elements; and a luminous plate comprises one or more electroluminescent surface light source plate deposited on a plate and a light transmitting plate which is fixed so as to cover the surface of the electroluminescent surface light source plate.

4. An ink feed measuring device as set forth in claim 1, wherein the light receiving plate is fixedly mounted on a base box with the mounting plate; and the luminous plate is fixedly mounted on a top cover via an elastic material layer placed on the rear surface of the luminous plate; and the top cover is openably supported with respect to the base box.

5. An ink feed measuring device as set forth in claim 4, wherein a mounting frame constructed in the shape of a picture frame is on the circumference of the luminous plate.

6. An ink feed measuring device as set forth in claim 1, wherein the coupled outputs are respectively added and are each fed to further amplifier stages.

7. An ink feed measuring device as set forth in claim 6, wherein an analog/digital converter is provided on the output side of the further amplifier stages, the analog/digital converter being constructed so that the output signals from the further amplifier stages are converted therein into digital signals.

* * * * *